US00PP08719P

United States Patent [19]

Zary

[11] Patent Number: Plant 8,719

[45] Date of Patent: May 10, 1994

[54] SHRUB ROSE PLANT NAMED 'JACCASP'

[75] Inventor: Keith W. Zary, Thousand Oaks, Calif.

[73] Assignee: Bear Creek Gardens, Inc., Medford, Oreg.

[21] Appl. No.: 42,113

[22] Filed: Apr. 2, 1993

[51] Int. Cl.[5] ..... A01H 5/00

[52] U.S. Cl. ..... Plt./1

[58] Field of Search ..... Plt. 1, 7.1, 9

*Primary Examiner*—Howard J. Locker

*Attorney, Agent, or Firm*—Klarquist, Sparkman, Campbell, Leigh and Whinston

[57] ABSTRACT

A shrub rose plant having recurrent blooms; dwarf procumbent habit of growth; small, dark green, glossy, disease-resistant foliage; heavy production of glands on the peduncle; and ease of propagation by softwood cuttings.

1 Drawing Sheet

The present invention relates to a new and distinct variety of rose plant of the shrub class which was originated by me by crossing the variety KORimro, with the variety of MACminmo, U.S. Plant Pat. No. 7,319.

The primary objective of this breeding was to produce a new rose variety having the procumbent growth habit of the once-flowering female parent combined with the recurrent flowering of the male parent. The objective was substantially achieved along with other desirable improvements as evidenced by the following unique combination of characteristics which are outstanding in the new variety and which distinguish it from its parents, as well as from all other varieties of which I am aware:

1. Dwarf procumbent habit of growth;
2. Dark green, glossy, disease-resistant foliage;
3. Recurrent bloom;
4. Presence of many glands on peduncles; and
5. Ease of propagation by softwood cuttings.

Asexual reproduction of this new variety by budding and by softwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORimro.

*Pollen parent.*—MACminmo, U.S. Plant Pat. No. 7,319.

Classification:

*Botanical.*—Rosa hybrida.

*Commercial.*—Shrub.

FLOWER

Observations made from specimens grown in a garden environment in Somis, Calif., from April through November, 1992.

Blooming habit: Recurrent.

Bud:

*Size.*—½ inch when the petals start to unfurl.

*Form.*—Short, globular.

*Color.*—When sepals first divide, bud color is Red Group 52C. When half blown, the upper and lower sides of the petals are Red Group 52C.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Apple. Size: Small (3/16×3/16 inch). Surface: Smooth.

*Peduncle.*—Length: Short (½ inch). Surface: Very glandular. Color: Medium green and bronzy. Strength: Stiff, erect, slender.

Bloom:

*Size.*—Small. Average open size is 1–1¼ inches.

*Borne.*—Singly and several together, in pyramidal clusters.

*Stems.*—Short (4–5 inches).

*Form.*—When first open: High centered. Permanence: Flattens, outer petals curl back.

*Petalage.*—Number of petals under normal conditions: 40–45.

*Color.*—The upper and reverse sides of the petals are Red Group 52C. The base of each petal has a yellowish half moon (⅛×⅛ inch) at the point of attachment. The major color on the upper side is Red Group 52C.

*Variegations.*—Often a white streak down the mid rib of the petals.

*Discoloration.*—No change in the general tonality at the end of the first day or at the end of the third day.

*Fragrance.*—Slight.

Petals:

*Texture.*—Thin.

*Shape.*—Deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: Short (3–4 days). As a cut flower: Short (3–4 days).

Reproductive parts:

*Anthers.*—Size: Small. Quantity: Many. Color: Yellow. Arrangement: Regular around styles.

*Filaments.*—Color: White.

*Pollen.*—Color: Lemon yellow.

*Styles.*—Color: Greenish white.

*Stigmas.*—Color: Greenish white.

Form: Shrub.

Growth: Vigorous, dwarf, sprawling, height in California 12–15 inches, width 24–30 inches.

Foliage: Number of leaflets on normal mid-stem leaves: 5.

*Size.*—Small (2×1 inch).

*Quantity.*—Abundant.

*Color.*—New foliage: Dark green, glossy. Old foliage: Dark green, glossy; Green Group 139A.

Leaflets:

*Shape.*—Broadly oval.

*Texture.*—Upper side: Leathery, glossy.

*Edge.*—Serrated.

*Serration.*—Single, large.

*Petiole rachis.*—Color: Green.

*Petiole underside.*—Smooth, with occasional prickles.

*Stipules.*—Medium, bearded.

*Disease resistance.*—Resistant to mildew and rust under normal growing conditions at Somis, Calif.

Wood:

*New wood.*—Color: Reddish green. Bark: Smooth.

*Old wood.*—Color: Green. Bark: Smooth.

Prickles:

*Quantity.*—On main canes from base and on laterals from main canes: Ordinary.

*Form.*—Hooked downward.

*Color when young.*—Red.

Small prickles:

*Quantity.*—On main stalks and on laterals: None.

I claim:

1. A new and distinct variety of rose plant of the shrub class, substantially as herein shown and described, characterized particularly as to novelty by the unique combination of its recurrent blooms; dwarf procumbent habit of growth; small, dark green, glossy, disease-resistant foliage; heavy production of glands on the peduncle; and ease of propagation by softwood cuttings.

* * * * *

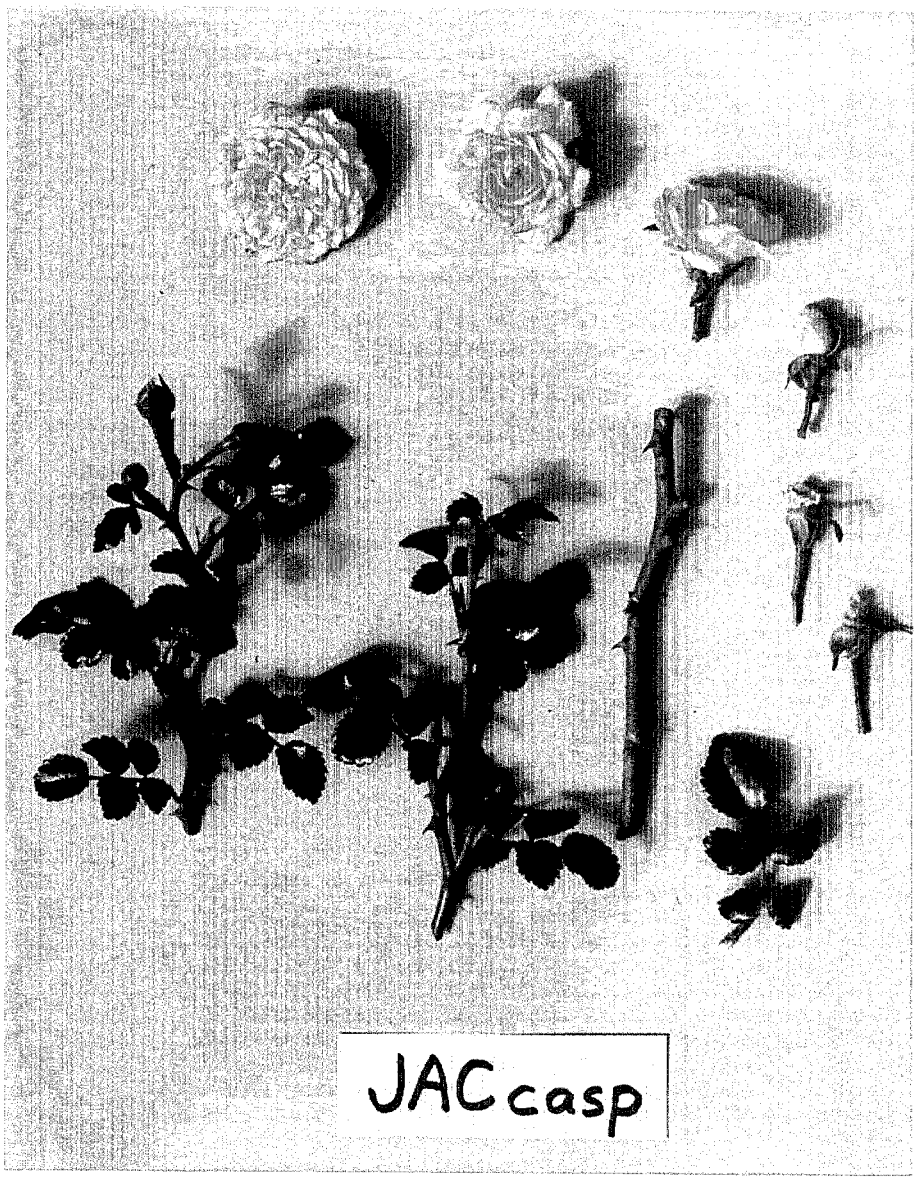
JAC casp